United States Patent
Matsumoto et al.

(10) Patent No.: US 6,472,168 B2
(45) Date of Patent: Oct. 29, 2002

(54) PROCESS FOR COUNTING SPERMS AND REAGENT THEREFOR

(75) Inventors: Teruya Matsumoto, Hyogo; Hiroshi Okada, Nishinomiya; Yukio Hamaguchi, Akashi, all of (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 09/790,368

(22) Filed: Feb. 22, 2001

(65) Prior Publication Data

US 2001/0024806 A1 Sep. 27, 2001

(30) Foreign Application Priority Data

Feb. 29, 2000 (JP) ........................................ 2000-052953

(51) Int. Cl.$^7$ ............................. C12Q 1/06; G01N 1/30; G01N 33/48; G01N 21/76; G01N 21/64
(52) U.S. Cl. ........................... 435/40.5; 435/39; 436/63; 436/172; 250/461.2
(58) Field of Search ................... 435/40.5, 39; 569/281; 436/63, 172; 250/461.2

(56) References Cited

U.S. PATENT DOCUMENTS 4,559,309 A 12/1985 Evenson et al.
5,985,572 A * 11/1999 Macfarlane

OTHER PUBLICATIONS

Takacs et al. 1987. ACTA Biochim. Biophys. Hung. vol. 22, No. 1, pp. 45–58, BIOSIS Abstract enclosed.*
Janos et al. 1986. Magy. Allatorv. Lapja. vol. 41, No. 8, pp. 459–463, BIOSIS Abstract enclosed.*
Omura et al., Usefulness of Particle Size Distribution Analyzer for Counting the Number of Sperm, Fukuoka Medical Journal, 88(8): 297–297.
Sasaki, et al., Simplified Method for Rapid Calculation of Sperm Numbers in Bull Semen Diluted with Extender Containing Egg Yolk by Automatic Blood Cell Counter, Journal of Studying Artificial Insemination, vol. 7, No. 2, May, 1985.

* cited by examiner

Primary Examiner—Christopher R. Tate
(74) Attorney, Agent, or Firm—Cohan, Pontani, Lieberman & Pavane

(57) ABSTRACT

A process for counting sperms (sperm cells) comprises the steps of: (1) mixing a specimen containing sperms with an aqueous solution containing a cationic surfactant in an amount effective in removing contaminants contained in the specimen to give a surfactant-treated specimen, (2) staining the sperms contained in the surfactant-treated specimen with a staining liquid containing a dye for staining nucleic acid to give a measuring specimen, (3) introducing the measuring specimen into a flow cell in a flow cytometer and irradiating the stained sperms in the measuring specimen with excitation light, (4) detecting a scattered light signal and a fluorescent light signal emitted from the sperms irradiated with the excitation light, (5) preparing a two-dimensional distribution involving two axes of a scattered light intensity and a fluorescent light intensity based on the scattered light signal and the fluorescent light signal, and (6) specifying a region of a sperm mass on the two-dimensional distribution and counting the number of sperm in the region of the sperm mass.

8 Claims, 3 Drawing Sheets

PROCESS FOR COUNTING SPERMS AND REAGENT THEREFOR

CROSS-REFERENCES TO RELATED APPLICATIONS

This application is related to Japanese Patent Application No. 2000-52953, filed on Feb. 29, 2000 whose priority is claimed under 35 USC § 119, the disclosures of which are incorporated by reference in their entirety.

BACKGROUND OF THE INVENTION

1. Field of the Invention

The present invention relates to a process for counting sperms (sperm cells) by the flow cytometry.

2. Related Art

For treating male infertility in the urology department, properties concerning fertility such as concentration, motility, teratosis of sperm in semen have been examined as a means for specifying the cause. It was recently reported that there was an inclination of decreasing a concentration and amount of sperm in male adults under influence of endocrine-disrupting chemicals. A number of sperm-related reports due to epidemiological investigations were made, but various results including positive and negative ones were present on lowering the sperm properties. Since there is no standardization of an assay of sperm concentration, credibility or statistical significance of those data is questionable.

Known methods of counting sperms in conventional semen examination include a method of using a hemocytometer as shown in the guideline issued by WHO, a method of observation with microscope by using a sperm counter by Markler Chember and so on. However, these methods have a problem that, since they mean a subjective method of counting sperms with eyes, the resultant data differ even between samples of the same origin, depending upon investigating institutes or inspectors. Moreover, such a method of counting sperms need so much time that it is not suitable for treating a large number of samples. In addition, there are some problems in accuracy and reproducibility, because semen shows so high viscosity that there occurs certain unevenness on the distribution of sperm cells, and because there are a very few number of sperm cells to be counted.

In order to overcome those problems, methods of counting sperms with an automatic homocytometer [Journal of Studying Artificial Insemination, Vol. 7, No. 2 May, 1985], an electric resistance type particle counter [Fukuoka Medical Journal, 88(8): 294–297] and a flow cytometer [U.S. Pat. No. 4,559,309] had already been tried.

Contaminants such as leukocyte, erythrocyte, granulocyte, bacteria, oil drops, etc. are often found in semen. It is pointed out that, also in trials of the automation, some errors have occurred in the counting data under the influence of these contaminants. In particular, such contaminants give so remarkable influence in assaying semen having a low concentration of sperms due to hypospermia that the number of sperms may hardly be determined accurately. Though some trials to avoid the influence of those contaminants with a trypsin and lipase solution were made, the effects were so insufficient that the number of sperms could hardly be determined accurately.

SUMMARY OF THE INVENTION

The present invention has been established in view of the circumstances as described above, and it is an object of the present invention to provide a process for accurately counting the number of sperms.

The present invention provides the process for counting sperms comprising the step of:

(1) mixing a specimen containing sperms with an aqueous solution containing a cationic surfactant in an amount effective in removing contaminants contained in the specimen to give a surfactant-treated specimen, (2) staining the sperms contained in the surfactant-treated specimen with a staining liquid containing a dye for staining nucleic acid to give a measuring specimen, (3) introducing the measuring specimen into a flow cell in a flow cytometer and irradiating the stained sperms in the measuring specimen with excitation light, (4) detecting a scattered light signal and a fluorescent light signal emitted from the sperms irradiated with the excitation light, (5) preparing a two-dimensional distribution involving two axes of a scattered light intensity and a fluorescent light intensity based on the scattered light signal and the fluorescent light signal, and (6) specifying a region of a sperm mass on the two-dimensional distribution and counting the number of sperm in the region of the sperm mass.

DESCRIPTION OF THE PREFERRED EMBODIMENTS

Figure 1:
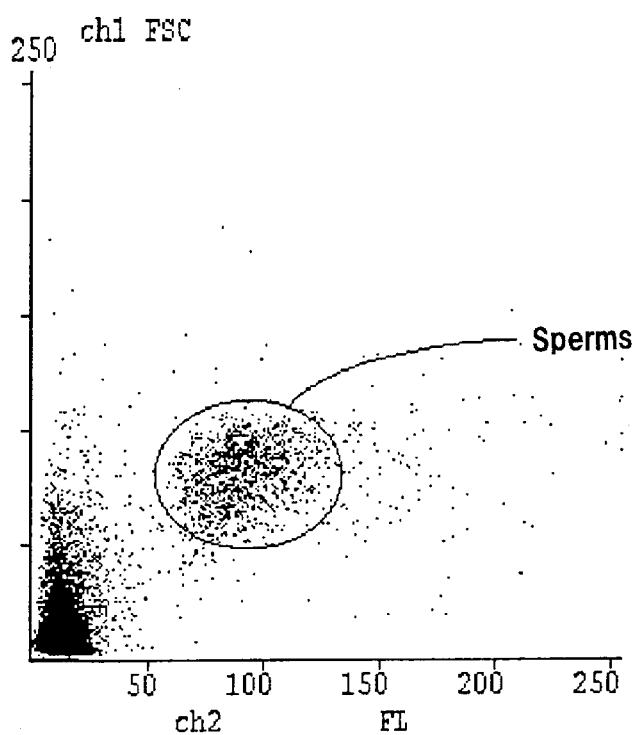
FIG. 1 shows the scattergram of the semen treated with the cationic surfactant in Example 1 of the present invention.

The specimen containing sperms used as an object to be measured in the present invention involves semen, urine, mixture thereof and homogenized testis of mammals.

The cationic surfactant of the present invention is used for removing contaminants such as leukocytes, erythrocytes, granulocytes, bacteria, tissue fragments, oily drops, etc. contained in a specimen containing sperms. As far as it can remove those contaminants, no particular limitation is needed for the cationic surfactant, but the quaternary ammonium salts and pyridinium salts as shown below can be used appropriately:

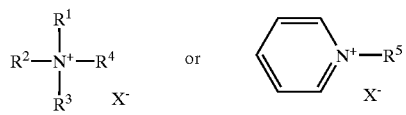

(wherein $R^1$, $R^2$ and $R^3$, the same or different, are hydrogen atom, a $C_{1-8}$ alkyl group or a $C_{6-8}$ aralkyl group; $R_4$ is a $C_{8-18}$ alkyl group, a $C_{8-18}$ alkenyl group or a $C_{6-18}$ aralkyl group; $R_5$ is a $C_{8-18}$ alkyl group; X is anion).

A $C_{1-8}$ alkyl group includes methyl, ethyl, propyl, butyl, pentyl, hexyl, heptyl, octyl, etc.

A $C_{6-8}$ aralkyl group includes benzyl, etc.

Among them, as $R_1$, $R_2$ and $R_3$, a $C_{1-3}$ alkyl group such as methyl ethyl, propyl, etc. is preferred.

A $C_{8-18}$ alkyl group includes octyl, decyl, dodecyl, tetradecyl etc.

A $C_{8-18}$ alkenyl group includes octenyl, decenyl, dodecenyl, etc.

A $C_{6-18}$ aralkyl group includes benzyl, phenetyl, etc.,

Among them, as $R_4$, and $R_5$, a $C_{10-18}$ liner alkyl group such as decyl, dodecyl, tetradecyl, etc. is preferred.

Examples of these cationic surfactants are dodecyltrimethylammonium chloride, tetradecyltrimethylammonium bromide, hexadecyltrimethylammonium chloride, hexadecylpyridinium chloride, hexadecyldimethylethylammonium bromide, benzyl dimethylhexadecylammonium chloride, octylammonium chloride etc. Among them, dodecyltrimethylammonium chloride, tetradecyltrimethylammonium bromide, hexadecyltrimethylammonium chloride, hexadecylpyridinium chloride, hexadecyldimethylethylammonium bromide, benzyl dimethylhexadecylammonium chloride are prefarable. These cationic surfactantmay be used sololy or as a mixture thereof (e.g., a mixture of dodecyltrimethylammonium chloride, hexadecyltrimethylammonium chloride and Octadecyltrimethylammonium chloride; a mixture of dodecyltrimethylammonium chloride and tetradecyltrimethylammonium bromide; a mixture of dodecyltrimethylammonium chloride and hexadecyltrimethylammonium chloride; a mixture of tetradecyltrimethylammonium bromide and hexadecyltrimethylammonium chloride, etc.)

Effective amount of the cationic surfactant for removing the contaminants may be 0.01–25 w/v % with respect to the measuring specimen (as a final concentration), preferably 0.5–15 w/v %, though it differs depending upon the kind of cationic surfactant to be used. For example, effective amount of dodecyltrimethylammonium chloride may be 0.1–20 w/v % as the final concentration, preferably 1.0–10 w/v %. As the carbon number of the hydrophobic moiety in the cationic surfactant increases, its necessary amount may decrease.

For removing the contaminants, the specimen containing sperms is simply mixed with an aqueous solution containing the cationic surfactant. The contacting of the sperms with the cationic surfactant may be carried out at a temperature in the range from room temperature to 40° C. for 5–120 sec. Accordingly, contaminants (cell components such as leukocytes) are hemolysed or shrank through the action of the cationic surfactant so that their forward scattered light intensity and forward fluorescent light intensity can be reduced. On the other hand, the shape of sperms is maintained so that they can easily be discriminated from the contaminants.

No special limitation is given to the nucleic acid-staining dye to be used in the present invention as long as it emits fluorescent light. In the case of using argon laser as a light source, at least one dye is selected from the group consisting of ethidium bromide, propidium iodide, N-methyl-4-(1-pyren)vinylpropidium iodide, TOTO-1, TOTO-3, YOYO-1, YOYO-3, BOBO-1, BOBO-3, ethidium homodimer-1 (EthD-1), ethidium homodimer-2 (EthD-2), POPO-1, POPO-3, BO-PRO-1, YO-PRO-1, TO-PRO-1, etc. These dyes may be used solely or as a mixture thereof. Further, these dyes are commercially available, for example, from Molecular Proves Co. Appropriate concentration of these dyes may be selected depending upon the kind of dye, and may be 0.1–100 ppm as the final concentration, preferably 30–60 ppm. When other laser having other wavelength is used as the light source, a dye as suitable for the wavelength may be used.

Moreover, other types of dyes, for example, a dye to stain a cell membrane can be used in combination with the nucleic acid-staining dye. No special limitation is given to the dye to stain the cell membrane as long as it emits fluorescent light. In the case of using argon laser as light source, for example, condensed benzene derivatives, in particular, oxacarbocyanine dyes DiOCn (3)(n=1–6), may be used, and DiOCC6(3) (3,3'-(di-n-hexyl)-2,2'-oxacarbocyanine iodide) is preferred. These dyes are available, for example, as NK-series of Nippon Photosensitive Dye Laboratory Ltd. Other preferable condensed benzene derivatives may illustratively include NK-91, NK-528, NL-97, Basic Yellow 11 and Basic Red 14. Appropriate concentration of the dye staining the cell membrane may be 0.1–50 ppm as the final concentration (concentration in the specimen to be measured), preferably 1–30 ppm. In the case of using other lasers having different wavelength as the light source, appropriate dyes for the wavelength can be used.

It is preferable to maintain suitable pH value of the specimen for staining the sperms. Therefore, a buffer capable of keeping pH 5.0–9.0, preferably 6.5–7.5 can be used. The buffer may be added to an aqueous solution of the cationic surfactant or a staining liquid containing the nucleic acid-staining dye. Examples of the buffer are HEPES, citrate, phosphate, phthalate, fumarate, glycine, lactate, succinate, Menzel buffer, Michaelis buffer, Britton Robinson buffer, MacIlvain buffer, etc.

The staining liquid may contain the nucleic acid-staining dye and the buffer in an aqueous solution, or may be composed of two liquids, an solution of the nucleic acid-staining dye dissolved in an aqueous organic solvent such as ethanol or ethylene glycol and a diluent containing the buffer. This diluent may contain the cationic surfactant.

The staining of the sperms may be carried out at a temperature in the range from room temperature to 40° C., preferably 33–37° C., for 5–120 sec, preferably 10–30 sec.

No special limitation is given to the flow cytometer to be used in the present invention as long as it has a light source capable of exciting the nucleic acid-staining dye to be used. In the case of using a dye capable of exciting at around 488 nm, for example, a flow cytometer using argon laser as the light source may be used. Examples thereof are commercially available devices such as FACScan (Becton Dickinson and Company), R Series (Sysmex Corporation), UF Series (Sysmex Corporation), etc. A flow cytometer having a light source applicable to the dye to be used can appropriately be selected.

Contaminants such as leukocytes, erythrocytes, granulocytes, bacteria, tissue fragments, oily drops and so on are dissolved by adding the cationic surfactant to the specimen containing the sperms. Cell membranes of the sperms are damaged to ready for easy absorption of the nucleic acid-staining dye into the cells. Then, DNA within the cells is stained by adding the nucleic acid-staining dye.

Scattered light and fluorescent light based on the dye bound to the DNA are emitted from the thus-stained sperms by introducing the specimen containing the stained sperms into flow cells of the flow cytometer and irradiating the stained sperms with the excitation light. Of the emitted scattered light, for example, forward scattered light and fluorescent light are detected to draw a two-dimensional distribution diagram having two axes of a forward scattered light intensity and a fluorescent light intensity. As a result, the cell mass is formed on the distribution diagram.

A region of the sperm cell mass is decided by gating to this cell mass, and then the cell number within this region is counted.

EXAMPLE

Practical embodiments of the present invention will be illustratively shown by the following examples, but they don't limit the scope of the present invention.

Example 1

Preparation of Aqueous Solution of Cationic Surfactant

| Dodecyltrimethylammonium chloride | 253.8 g |
|---|---|
| Hexadecyltrimethylammonium chloride | 16.2 g |
| Octadecyltrimethylammonium chloride | 4.5 g |
| Isopropyl alcohol | 30 ml |
| Purified water | 1 L |

A solution of octadecyltrimethylammonium chloride in isopropyl alcohol was added to purified water together with dodecyltrimethylammonium chloride and hexamethyltrimethylammonium chloride to give an aqueous solution of a cationic surfactant.

Preparation of Staining Liquid

| Preparation of staining liquid: | |
|---|---|
| 3,3'-(Di-n-hexyl)-2,2'-oxacarbocyanine iodide | 400 ppm |
| Ethidium bromide | 1600 ppm |
| Ethylene glycol was used as a solvent. | |
| Preparation of diluent: | |
| HEPES | 50 mM |
| Sodium hydroxide | up to pH 7.0 |
| Sodium propionate | 60 mM |
| EDTA-3K | 4.0 g/L |
| Purified water | 1 L |

The above-listed ingredients were dissolved in purified water.

Measurement of Semen

To 40 µl of semen (collected from a man with normal health and then preserved at room temperature in a sealed container; measured within 24 hours after collection) was added 360 µl of the aqueous solution of the cationic surfactant, and the mixture was stirred for 10 sec. Then, 1160 µl of the diluent and 40 µl of the staining liquid were added, and the resultant mixture was incubated at 37° C. for 10 sec. Forward scattered light intensity (FSC) and forward fluorescent light intensity (FL) were measured with a flow cytometer (UF-100, Sysmex Corporation) using argon laser as a light source, and two-dimensional distribution diagram (scattergram) including two axes of the forward scattered light intensity and the forward fluorescent light intensity was prepared. FIG. 1 shows the result.

Further, as control, semen was diluted with physiological saline in place of treating semen with the cationic surfactant. The result is shown in FIG. 2.

Figure 2:
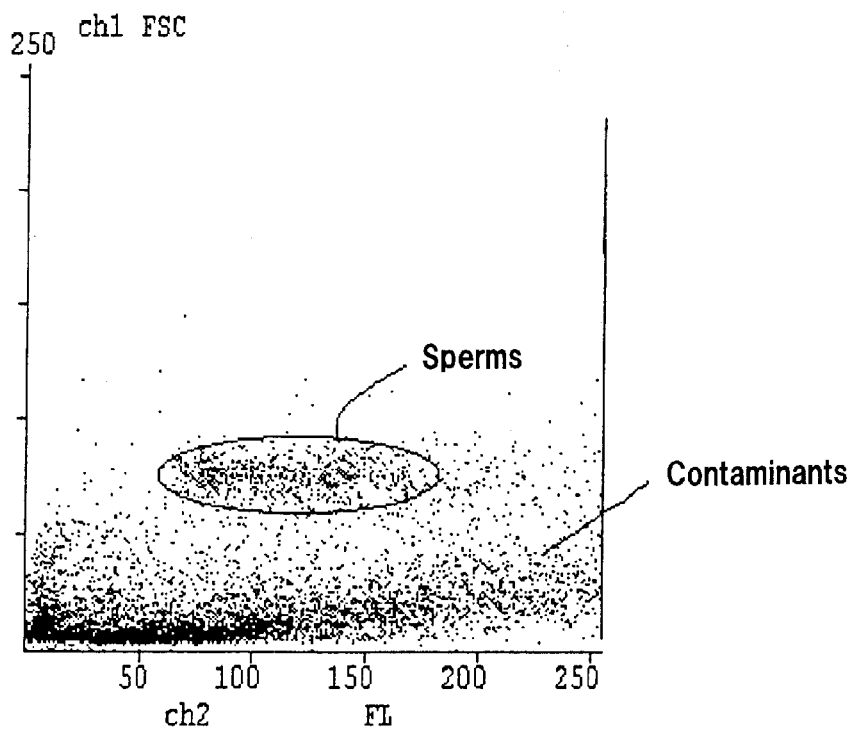
FIG. 2 shows the scattergram of the semen diluted with physiological saline instead of the surfactant in Example 1 of the present invention.

As shown in FIG. 1, the contaminants spread over a region showing low forward scattered light intensity in FIG. 2 were removed, the sperm cell mass was closely united, and the region of the sperm cell mass was easily specified by treating the semen with the cationic surfactant.

Example 2

Semen containing contaminants such as erythrocyte, leukocyte, etc. was treated with the surfactant, stained and measured in the same manner as in Example 1 to prepare the two-dimensional distribution diagram (scattergram) including two axes of the forward scattered light intensity and forward fluorescent light intensity. The result is shown in FIG. 3.

Further, as control, semen was treated with physiological saline instead of treating it with the cationic surfactant. The result is shown in FIG. 4.

Figure 3:
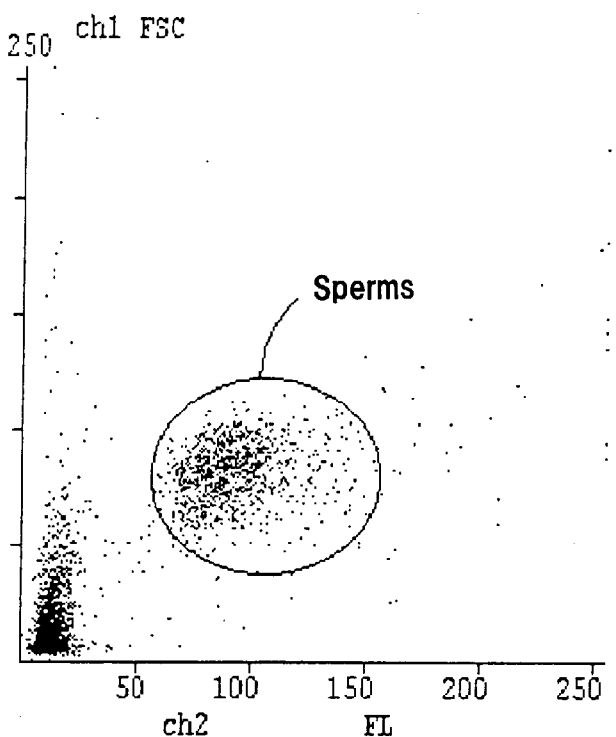
FIG. 3 shows the scattergram of the semen containing contaminants such as erythrocytes, leukocytes, etc. treated with the cationic surfactant in Example 2 of the present invention.
Figure 4:
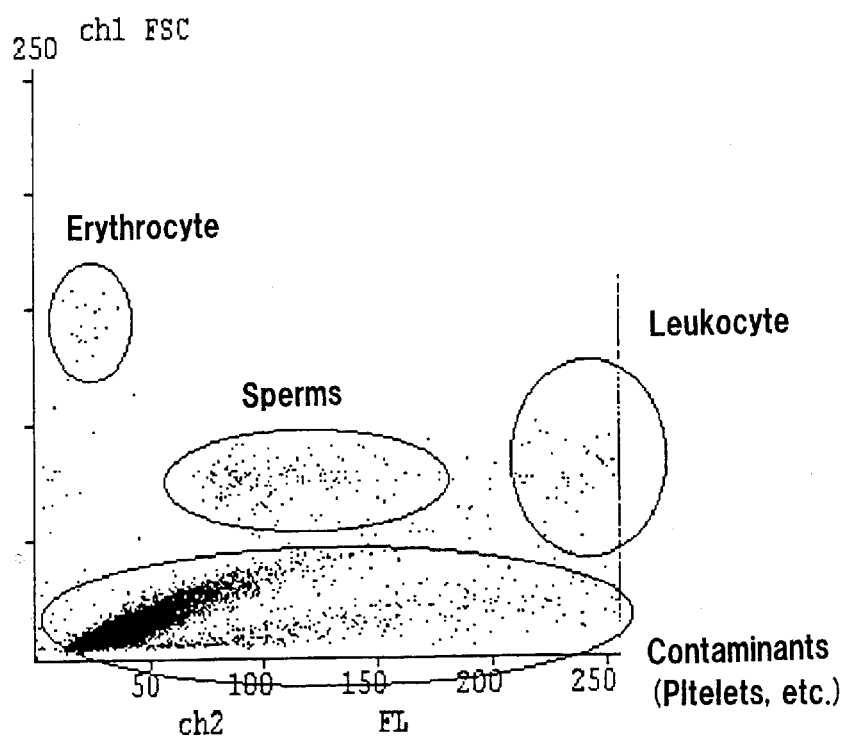
FIG. 4 shows the scattergram of the semen diluted with physiological saline instead of the surfactant in Example 2 of the present invention.

As shown in FIG. 3, the leukocytes spread over a region showing high forward fluorescent light intensity, the erythrocytes existing in a region showing high forward scattered light intensity and low forward fluorescent light intensity, and the contaminants extended over a region showing low forward scattered light intensity as shown in FIG. 4 were removed by treating semen with the cationic surfactant. Further, the sperm cell mass was closely united, and the region of the sperm cell mass was easily specified.

Example 3

Linearity Test

Figure 5:
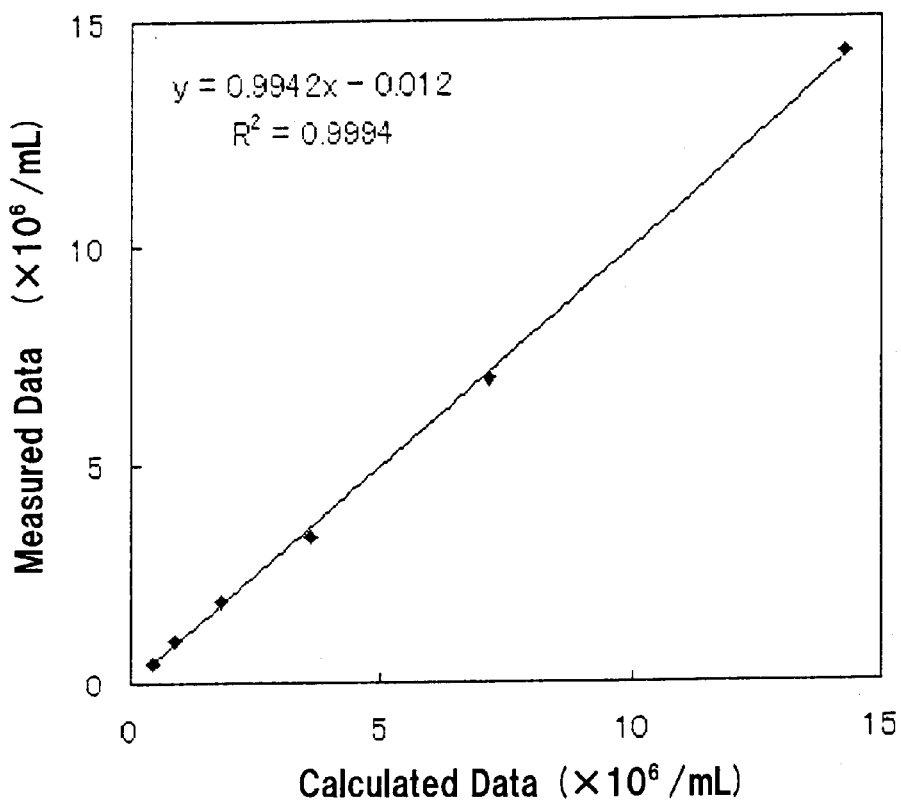
FIG. 5 shows the result of the linearity test in Example 3.

Semen samples were diluted with physiological saline to 2, 4, 8, 16 and 32 times, respectively, and the resultant specimens were treated with the surfactant, stained and measured in the same manner as in Example 1. Calculated data were compared with measured data. The result is shown in FIG. 5.

The measured data were almost the same as calculated data.

Example 4

Correlation with Visual Observation

Figure 6:
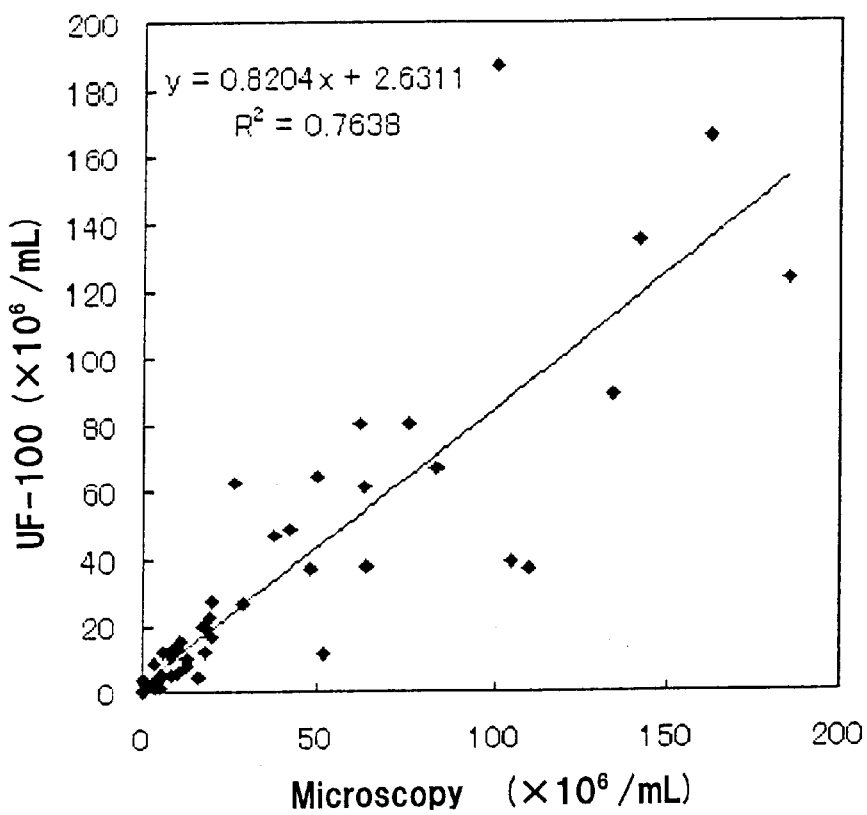
FIG. 6 shows the correlation between the results of Example 4.

In comparison with the results of the microscope method (Makler Chember method), 64 semen specimens were treated with the same reagent and in the same manner as in Example 1. As shown in FIG. 6, favorable correlation was obtained.

According to the present invention, it becomes possible to count the number of the sperms very accurately even in the semen specimen containing a number of contaminants.

Further, the number of the sperms in a specimen of low sperm concentration can also be counted with high accuracy.

What is claimed is:

1. A process for counting sperms comprising the steps of:
   (1) mixing a specimen containing sperms with an aqueous solution containing a cationic surfactant in an amount effective in removing contaminants contained in the specimen to give a surfactant-treated specimen,
   (2) staining the sperms contained in the surfactant-treated specimen with a staining liquid containing a dye for staining nucleic acid to give a measuring specimen,
   (3) introducing the measuring specimen into a flow cell in a flow cytometer and irradiating the stained sperms in the measuring specimen with excitation light,
   (4) detecting a scattered light signal and a fluorescent light signal emitted from the sperms irradiated with the excitation light,
   (5) preparing a two-dimensional distribution involving two axes of a scattered light intensity and a fluorescent light intensity based on the scattered light signal and the fluorescent light signal, and
   (6) specifying a region of a sperm mass on the two-dimensional distribution and counting the number of sperm in the region of the sperm mass.

2. A process for counting sperms according to claim 1, wherein the cationic surfactant is at least one kind selected from the group consisting of the quaternary ammonium salt and pyridinium salt as described below:

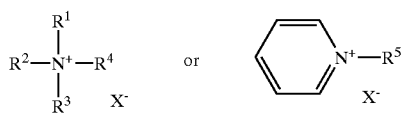

wherein $R_1$, $R_2$ and $R_3$, the same or different each other, are hydrogen atom, a $C_{1-8}$ alkyl group or a $C_{6-8}$ aralkyl group; $R_4$ is a $C_{8-18}$ alkyl group, a $C_{8-18}$ alkenyl group or a $C_{6-18}$ aralkyl group; $R_5$ is a $C_{8-18}$ alkyl group; X is anion.

3. A process for counting sperms according to claim 2, wherein the cationic surfactant is at least one kind selected from the group consisting of dodecyltrimethylammonium chloride, octadecyltrimethylammonium, tetradecyltrimethylammonium bromide, hexadecyltrimethylammonium chloride, hexadecylpyridinium chloride, hexadecyldimethylethylammonium bromide and benzyl dimethylhexadecylammonium chloride.

4. A process for counting sperms according to claim 3, wherein the cationic surfactant is a mixture of dodecyltrimethylammonium chloride, hexadecyltrimethylammonium chloride and octadecyltrimethylammonium chloride.

5. A process for counting sperms according to claim 1, wherein the amount of the cationic surfactant effective in removing the contaminants is 0.01–25 w/v % with respect to the measuring specimen.

6. A process for counting sperms according to claim 1, wherein the nucleic acid-staining dye is at least one kind selected from the group consisting of the following nucleic acid-staining dyes: ethidium bromide, propidium iodide, N-methyl-4-(1-pyren)vinyl-propidium iodide, 3,3'-(Di-n-hexyl)-2,2'-oxacarbocyanine iodide, TOTO-1, TOTO-3, YOYO-1, YOYO-3, BOBO-1, BOBO-3, ethidium homodimer-1 (EthD-1), ethidium homodimer-2 (EthD-2), POPO-1, POPO-3, BO-PRO-1, YO-PRO-1 and TO-PRO-1.

7. A process for counting sperms according to claim 6, wherein the nucleic acid-staining dye is used as a mixture of 3,3'-(Di-n-hexyl)-2,2'-oxacarbocyanine iodide and Ethidium bromide.

8. A process for counting sperms according to claim 6, wherein the nucleic acid-staining dye is used in a concentration of 0.1–100 ppm with respect to the measuring specimen.

* * * * *